United States Patent [19]

Patelli et al.

[11] 4,046,878
[45] Sept. 6, 1977

[54] DAUNOMYCIN ANALOGUES, THEIR PREPARATION AND USE

[75] Inventors: Bianca Patelli; Luigi Bernardi, both of Milan; Federico Arcamone, Nerviano (Milan); Aurelio Di Marco, Milan, all of Italy

[73] Assignee: Societa' Farmaceutici Italia S.p.A., Milan, Italy

[21] Appl. No.: 579,901

[22] Filed: May 22, 1975

[30] Foreign Application Priority Data

June 12, 1974 United Kingdom ............ 26083/74

[51] Int. Cl.² .................. A61K 31/71; C07H 11/00
[52] U.S. Cl. ........................ 424/180; 536/4; 536/17; 536/18
[58] Field of Search .............. 260/210 AB, 210 R; 424/180; 536/4, 17

[56] References Cited

U.S. PATENT DOCUMENTS

| | | | |
|---|---|---|---|
| 3,427,300 | 2/1969 | Sarett et al. | 260/210 R |
| 3,686,163 | 8/1972 | Arcamone et al. | 260/210 R |
| 3,803,124 | 4/1974 | Arcamone et al. | 260/210 AB |

Primary Examiner—Johnnie R. Brown
Attorney, Agent, or Firm—Hubbell, Cohen, Stiefel & Gross

[57] ABSTRACT

Daunomycin analogues of the formula:

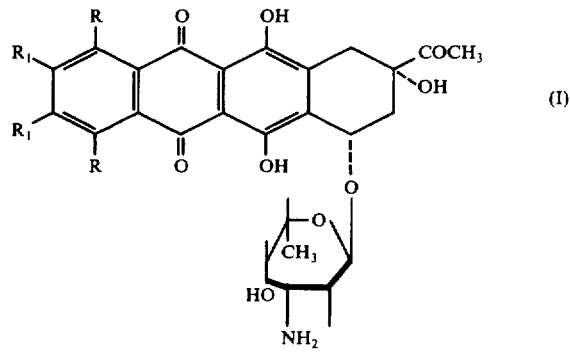

wherein when each $R_1$ is hydrogen, each R is hydrogen, chlorine, bromine, methyl or methoxy and when each $R_1$ is chlorine, bromine or methyl, each R is hydrogen, are useful in treating various mammalian tumors and are prepared by reacting a daunomycinone derivative of the formula:

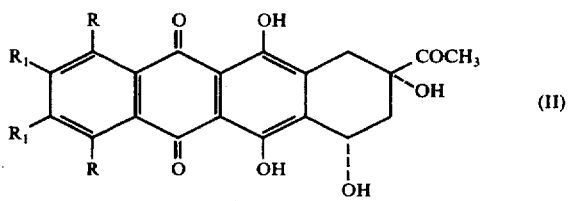

wherein R and $R_1$ are as defined above with 1-chloro-2,3,6-trideoxy-3-trifluoroacetamido-4-trifluoroacetoxy-α-L-lyxopyranose in an inert anhydrous organic solvent in the presence of a catalyst and a hydrogen chloride acceptor.

20 Claims, No Drawings

DAUNOMYCIN ANALOGUES, THEIR PREPARATION AND USE

CROSS REFERENCE TO RELATED APPLICATIONS

This application is related to and incorporates by reference the contents of application Ser. No. 560,105, filed Mar. 19, 1975 in the names of Federico Arcamone, Aurelio Di Marco and Sergio Penco and entitled DAUNOMYCINS, PROCESS FOR THEIR PREPARATION AND USES THEREOF, said application being owned by the unrecorded assignee hereof.

BACKGROUND OF THE INVENTION

1. Field of the Invention

The present invention relates to novel analogues of the known antibiotic daunomycin, processes for their preparation and the use thereof in treating various mammalian tumors.

2. The Prior Art

British pat. No. 1,003,383 which is owned by the unrecorded assignee hereof describes and claims the antibiotic daunomycin.

SUMMARY OF THE INVENTION

The present invention provides, in one aspect thereof, a new class of daunomycin analogues having the formula:

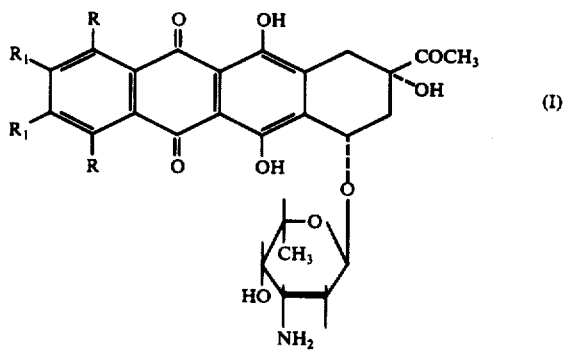

wherein when each $R_1$ is hydrogen, each R is hydrogen, chlorine, bromine, methyl or methoxy, and when each $R_1$ is chlorine, bromine or methyl, each R is hydrogen.

The present invention also provides a process for the preparation of these daunomycin analogues which comprises condensing 1-chloro-2,3,6-trideoxy-3-trifluoroacetamido-4-trifluoroacetoxy-α-L-lyxopyranose with an anthracyclinone, i.e., a daunomycinone derivative of the formula:

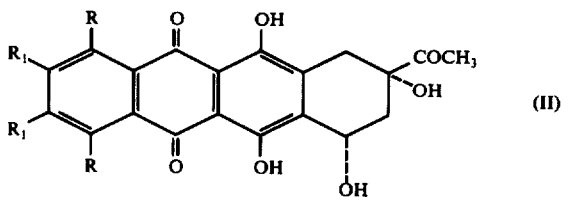

wherein R and $R_1$ are as defined above in an anhydrous solvent, such as chloroform or methylene dichloride or dimethyl formamide, nitromethane, toluene or acetonitrile in the presence of a catalyst comprising a mercuric halide, for example, mercuric bromide; a hydrogen chloride acceptor, for example, mercuric oxide, silver carbonate, silver oxide or cadmium carbonate; and a molecular seive, for example 5 A molecular sieve, to give a trifluoroacetyl protected derivative of the compound of formula (I) which, after treatment with methanol and then with an alkali such as sodium hydroxide, is converted to the desired compound.

When the starting anthracyclinone is a racemic material, for example, 4-demethoxydaunomycinone (R = $R_1$ = H), the reaction product is a racemic mixture in which each component of the race mate is in turn a mixture of the α and β anomers. Thus, when starting with 4-demethyldaunomycinone, one obtains a racemic mixture of (−)-daunosaminyl(-)4-demethoxydaunomycinone (α+βanomers) and (−) daunosaminyl (+) 4-demethoxydaunomycinone (α+β anomers) which racemate can then be separated according to conventional techniques. Alternatively the racemic mixture can be employed without resolution in the treatment of neoplastic diseases.

The preparation of 1-chloro-2,3,6-trideoxy-3-trifluoroacetamido-4-trifluoroacetoxy-α-L-lyxopyranose, as well as a more detailed description of the condensation reaction between it and the daunomycinone derivative (II) is set forth in the copending application referred to above and which is incorporated herein by reference.

Among the new compounds of formula (I) according to the invention, there are included the following:

(−)daunosaminyl(−)1,4-dimethyl-4-demethoxydaunomycinone; (−)daunosaminyl(+)1,4-dimethyl-4-demethoxydaunomycinone; (−)daunosaminyl(−)1-methoxydaunomycinone; (−)daunosaminyl(+)1-methoxydaunomycinone; (−)daunosaminyl(−)1,4-dichloro-4-demethoxydaunomycinone; (−) daunosaminyl(+)1,4-dichloro-4-demethoxydaunomycinone; (−)daunosaminyl(−)1,4-dibromo-4-demethoxydaunomycinone; (−)daunosaminyl(+)1,4-dibromo-4-demethoxydaunomycinone; (−)daunosaminyl(−)2,3-dimethyl-4-demethoxydaunomycinone; (−)daunosaminyl(+)2,3-dimethyl-4-demethoxydaunomycinone; (−)daunosaminyl(−)2,3-dichloro-4-demethoxydaunomycinone; (−)daunosaminyl(+)2,3-dichloro-4-demethoxydaunomycinone; (−)daunosaminyl(−)2,3-dibromo-4-demethoxydaunomycinone; (−)daunosaminyl(+)2,3-dibromo-4-demethoxydaunomycinone. It is, of course, to be understood that in each case, the compound (having either (7 S : 9 S) or (7 R : 9 R) configuration) is a mixture of α and β anomers. The notations (7 S : 9 S) and (7 R : 9 R) which indicate (+) and (−) respectively in the aglyconone names given above are in accordance with the literature wherein S=sinister and R=rectus; see, e.g., Cahn et al, Experientia, 1956 12, 81.

Finally, the invention also provides a method of inhibiting the growth of certain mammalian tumors such as ascites sarcoma 180 and $L_{1210}$ leukemia by administering therapeutically effective amounts of the compounds of the invention to animals afflicted with such tumors.

DESCRIPTION OF THE PREFERRED EMBODIMENTS

The process according to the invention is illustrated by the following preparative example wherein all parts given are by weight unless otherwise indicated.

EXAMPLE

Preparation of (−)daunosaminyl(−)4-demethoxydaunomycinone (α+β anomers) and (−)daunosaminyl(+)4-demethoxydaunomycinone (α+β anomers)

1.2 g 4-demethoxydaunomycinone-7-methyl ether (prepared according to the procedure described in C. M. Wong, Canadian Journal of Chemistry, 1971, 49, 2712) were dissolved in 22 ml. of trifluoroacetic acid and left standing overnight at room temperature, after which the solution was evaporated in vacuo to form a residue which was taken up in 50 ml. of acetone to which 10 ml. of 5% aqueous sodium bicarbonte were added. After 30 minutes, the solvent was evaporated off in vacuo, and the resulting residue taken up in chloroform and washed with water. Evaporation of the chloroform left a residue that was chromatographed on silica gel to give 0.475 g. of (+)4-demethoxydaunomycinone, m.p. 152°-155° C. This material produced a single spot at Rf = 0.44 when subjected to thin layer chromatography on silica gel using 80/20 (vol.) chloroform/acetone as elunet.

0.3 g. of (+)4-demethoxydaunomycinone was dissolved in 75 ml. of anhydrous chloroform, and 0.6 g. of mercuric oxide, 0.15 g. of mercuric bromide and 5 g. of 5 A molecular sieve were added thereto with stirring. After one hour, 0.7 g. of 1-chloro-2,3,6-trideoxy-3-trifluoroacetamido-4-trifluoroacetoxy-α-L-lyxopyranose was added and the suspension was stirred at room temperature for 16 hours. After filtration, the solution was concentrated in vacuo to form a residue which was then dissolved in 200 ml. of methanol and refluxed for 15 minutes. After evaporation of the methanol, the residue was chromatographed on a silica gel column using, as the elution solvent chloroform:benzene:methanol:100:20:3 (vol.) a first fraction of 0.270 g. of a mixture of the α-anomers of (−)daunosaminyl(−)4-demethoxydaunomycinone and (−)daunosaminyl (+)4-demethoxydaunomycinone in the form of the N-trifluoroacetyl derivatives (single spot on silica gel plates Rf = 0.34; chloroform:acetone 80:20 (vol.)), and a second fraction of 0.150 g. of a mixture of the β-anomers of (−)daunosaminyl(−)4-demethoxydaunomycinone and (−)daunosaminyl(+)4-demethoxydaunomycinone in the form of the N-trifluoroacetyl derivatives were obtained.

0.170 g. of the α-anomer mixture of (−)-daunosaminyl(−)4-demethoxydaunomycinone and (−)daunosaminyl(+)4-demethoxydaunomycinone in the form of the N-trifluoroacetyl derivatives was dissolved in 15 ml. of 0.1 ml. of 0.1N NaOH and left standing for 30 minutes at room temperture. The pH was adjusted at 8.6 with HCl and the solution was then repeatedly extracted with chloroform. The combined chloroform extracts were concentrated in vacuo to form a residue which was taken up in 5 ml. of methanol and acidified at pH 4.5 with 0.1N methanolic HCl. Ethyl ether was added to effect precipitation of the hydrochlorides of the α-anomer mixture of (−)daunosaminyl(−)4-demethoxydaunomycinone and (−)daunosaminyl(+) 4-demethoxydaunomycinone (the miture of hydrochlorides gave a single spot (Rf = 0.16) on silica gel plates using dichloromethane:methanol:water 100:20:2 (vol.)).

Following the same procedure, the β-anomer mixture of the N-trifluoroacetyl derivtives of (−) daunosaminyl(−)4-demethoxydaunomycinone and (−)daunosaminyl(+)4-demethoxydaunomycinone yield a mixture of the hydrochlorides of the β-anomers of (−) daunosaminyl(−)4-demethoxydaunomycinone and (−)daunosaminyl(+)4-demethoxydaunomycinone (the mixture of hydrochlorides gave a single spot (Rf = 0.14) on silica gel plates using dichloromethane:methanol:water 100:20:2 (vol.)).

The other novel daunomycin analogues of formula (I) of the invention can be prepared in the same manner by condensing the appropriate daunomycinone derivative of the formula (II).

BIOLOGICAL ACTIVITY

In the pharmacological evaluation tests, which are hereinafter described, the term "Test Compound" is used to indicate the mixture of the α-anomers of (−)daunosaminyl(+)4-demethoxydaunomycinone prepared in accordance with the above example.

PHARMACOLOGY

Effect of the Test Compound on the viability of HeLa cells

In vitro studies were carried out on HeLa cells, maintained in Eagle medium supplemented with 10% calf serum. The cells were treated with daunomycin, adriamycin* and the Test Compound for different periods of times. The cell viability was assessed by cells and seeding of 200-300 cells/plate. Colony numbers were evaluated 6 days later. As can be seen from the data in Table 1, the Test Compound is as active as adriamycin after 2 hours of treatment. After 8 hours of treatment, the inhibition of cell viability by the Test Compound is higher than the inhibition by either adriamycin or daunomycin.

* Adriamycin — a known antibiotic, the preparation of which is described in British Pat. Nos. 1,161,278 and 1,217,133 owned by the unrecorded assignee hereof.

Table 1

| Compound | ID 50 (μg/ml) | |
|---|---|---|
| | 2 hrs. | 8 hrs. |
| Daunomycin | 0.095 | 0.023 |
| Adriamycin | 0.2 | 0.039 |
| Test Compound | 0.2 | 0.002 |

*Adriamycin - a known antibiotic, the preparation of which is described in British Patents Nos. 1,161,278 and 1,217,133 owned by the unrecorded assignee hereof.

In vitro test on the formation of foci by Moloney Sarcoma Virus (MSV).

The Test Compound was evaluated in comparison with adriamycin on mouse embryo fibroblast cultures infected with MSV.

After treatment of 3 days, the % of inhibition as compared with controls was evaluated on cell proliferation in (cytotoxic cultures (cytotoxid activity) and on MSV foci formation in infected cultures (antiviral activity). The results as shown in Table 2, indicate a lesser antiviral activity than adriamycin and the same cytotoxic activity as adriamycin.

Table 2

| Compound | Doses (γ/ml) | % Foci (control = 100) | % Cells (control = 100) |
|---|---|---|---|
| Adriamycin | 0.0250 | 0 | 29 |
| | 0.0125 | 0 | 30 |
| | 0.006 | 26 | 53 |
| Test Compound | 0.6 | 0 | 0 |
| | 0.1 | 0 | 4.6 |
| | 0.0250 | 12 | 38 |
| | 0.006 | 54 | 46 |

The in vivo antitumor activity of the Test Compound was also studied in certain mouse tumors both in the solid and ascitic forms.

1. Ascitic tumors

Tests were carried out on groups of 10 mice (Swiss CD 1) inoculated intraperitoneally with $1 \times 10^6$ ascites sarcoma 180 cells/aminal. The animals were treated intraperitoneally with different concentrations of the Test Compound and adriamycin once a day following tumor implantation.

The results, summarized in Table 3, show that the Test Compound has a remarkable effect on ascitic tumor growth; i.e., the average survival time of the treated animals shows a considerable increase over untreated animals (arbitrarily designated as having an average survival time of 100).

The compound is active at lower doses than adriamycin.

Table 3

| Compound | Dose mg/kg day | % T/C* Increase in average survival time** | | |
|---|---|---|---|---|
| | | Experiment 1 | Experiment 2 | Experiment 3 |
| Test Compound | 0.12 | | | 115(0/10) |
| | 0.2 | | 146(0/10) | |
| | 0.25 | | | 188(1/10) |
| | 0.5 | | | 181(0/10) |
| | 1 | 185(0/10) | 107(0/10) | 223(1/10) |
| | 1.5 | | 79(0/10) | |
| | 2 | 61(1/10) | | |
| | 5 | 38(0/10) | | |
| Adriamycin | 0.1 | | | 100(0/10) |
| | 0.2 | | 107(0/10) | |
| | 1 | 146(1/9) | 143(1/10) | 169(1/9) |
| | 2 | 400(5/10) | | |
| | 5 | 311(4/10) | 225(1/10) | |
| | 10 | | 193(0/10) | |

*% T/C = (mean survival time of treated mice/mean survival time of control mice) × 100.
**The figures in parentheses indicate the number of longterm survivors, i.e., after 60 days. (1/10) indicates that out of a group of 10 test animals, one animal remained alive at the end of 60 days.

(*) % T/C = (mean survival time of treated mice/mean survival time of control mice) × 100. (**) The figures in parentheses indicate the number of longterm survivors, i.e., after 60 days. (1/10) indicates that out of a group of 10 test animals, one animal remained alive at the end of 60 days. 2. Solid tumors In vivo tests on the activity of the Test Compound as compared with adriamycin on solid tumors were carried out on groups of ten Swiss CD 1 mice subcutaneously grafter with fragments of neoplastic tissue and treated intravenously with the respective antibiotics for five days starting form the day following the tumor implantation.

On the tenth day, all the test animals were sacrificed and their tumors removed and weighed. The results given in Table 4 show that the higher non toxic dose tested (1 mg/kg) causes a 50% inhibitition of the tumor growth. The therapeutic index (T.I.) (*) calculated as = Maximum Tolerated dose (LD 10)/Minimum effective dose (T/C 0.10) is 3.7 for the Test Compound and 1.8 for adriamycin respectively.

Table 4

| Compound | Dose mg/kg | Tumor Weight | % T/C ** | Toxicity |
|---|---|---|---|---|
| Control | — | 3.036 | | |
| Test Compound | 0.5 | 2.295 | 76% | 0/10 |
| | 1 | 1.550 | 51 | 0/10 |
| | 2 | 0.485 | 16 | 3/10 |
| Adriamycin | 2.5 | 1.465 | 48% | 0/10 |

Table 4-continued

| Compound | Dose mg/kg | Tumor Weight | % T/C ** | Toxicity |
|---|---|---|---|---|
| | 3.5 | 0.364 | 12 | 7/10 |

*The therapeutic index (T.I) is expressed as the ratio between the maximum tolerated dose (LD$_{10}$) and the minimum effective dose, according to Skipper and Schmidt, Cancer Chemother. Rep. 17 : 1–128, 1962. The minimum effective dose indicates the dose which reduces by 90% the weight of tumors compared to controls : such 90% reduction correponds to a T/C value of 0.10 or 10%.
**% T/C = (mean tumor weight of treated mice/mean tumor weight of control mice) × 100.

(*) The therapeutic index (T.I.) is expressed as the ratio

Leukemia

The activity of the Test Compound was tested on BDF 1 mice inoculated intraperitoneally with $1 \times 10^5$ L 1210 leukemia cells/animal.

The animals were treated once, the day after tumor implantation. The results given in Table 5 show that at the non toxic doses tested, the average survival time of the treated animals increased considerably.

The Test Compound is seen to be active at lower doses than adriamycin.

Table 5

| Compound | Dose mg/kg | Average Survival Time | % T/C* | Toxicity |
|---|---|---|---|---|
| Control | — | 8 | | |
| Test Compound | 0.75 | 12.5 | 156 | 0/10 |
| | 1.5 | 13 | 162 | 1/10 |
| | 3 | 7 | 87 | 7/10 |
| Adriamycin | 2.5 | 12.5 | 156 | 0/10 |
| | 5 | 14 | 175 | 0/10 |
| | 10 | 16 | 200 | 4/10 |

*% T/C = (mean survival time of treated mice/mean survival time of control mice) × 100.

(*) % T/C = (mean survival time of treated mice/mean survival time of control mice) × 100.

Variations can, of course, be made without departing from the spirit and scope of the invention.

Having thus described our invention, what we desire to secure by Letters Patent and hereby claim is:

1. A racemic daunomycin analogue of the formula

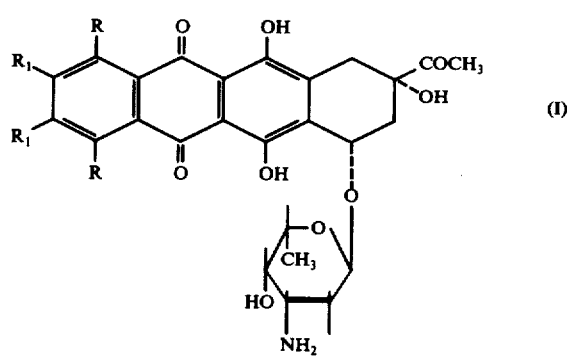

comprising the α-anomer, the β-anomer or a mixture of α- and β-anomers wherein when each $R_1$ is hydrogen, each R is hydrogen, chlorine, bromine methyl or methoxy; and when each $R_1$ is chlorine, bromine or methyl, each R is hydrogen.

2. A compound according to claim 1, which is (−)daunosaminyl (−)1,4-dimethyl-4-demethoxydaunomycinone (α- and β-anomers).

3. A compound according to claim 1, which is (−)daunosaminyl (+)1,4-dimethyl-4-demethoxydaunomycinone (α- and β-anomers).

4. A compound according to claim 1, which is (−)daunosaminyl (−)1-methoxydaunomycinone (α- and β-anomers).

5. A compound according to claim 1, which is (−)daunosaminyl(+)1-methoxydaunomycinone (α- and β-anomers).

6. A compound according to claim 1, which is (−)daunosaminyl(−)1,4-dichloro-4-demethoxydaunomycinone (α- and β-anomers).

7. A compound according to claim 1, which is (−)daunosaminyl (+)1,4-dichloro-4-demethoxydaunomycinone (α- and β-anomers).

8. A compound according to claim 1, which is (−)daunosaminyl (−)1,4-dibromo-4-demethoxydaunomycinone (α- and β-anomers).

9. A compound according to claim 1, which is (−)daunosaminyl (+)1,4-dibromo-4-demethoxydaunomycinone (α- and β-anomers).

10. A compound according to claim 1, which is (−)daunosaminyl(−)2,3-dimethyl-4-demethoxydaunomycinone (α- and β-anomers).

11. A compound according to claim 1, which is (−)daunsoaminyl(+)2,3-dimethyl-4-demethoxydaunomycinone (α- and β-anomers).

12. A compound according to claim 1, which is (−)daunosaminyl(−)2,3-dichloro-4-demethoxydaunomycinone (α- and β-anomers).

13. A compound according to claim 1, which is (−)daunosaminyl)−)2,3-dichloro-4-dichloro-4-demethoxydaunomycinone (α- and β-anomers).

14. A compound according to claim 1, which is (−)daunosaminyl(−)2,3-dibromo-4-demethoxydaunomycinone (α- and β-anomers).

15. A compound according to claim 1, which is (−)daunsoaminyl(+)2,3-dibromo-4-dibromo-4-demethoxydaunomycinone (α- and β-anomers).

16. A compound according to claim 1, which is (−)daunosaminyl(−)4-demethoxydaunomycinone (α- and β-anomers).

17. A compound according to claim 1, which is (−)daunosaminyl(+)4-demethoxydaunomycinone (α- and β-anomers).

18. A method of inhibiting the growth of a tumor selected from the group consisting of Moloney Sarcoma Virus, Sarcoma 180 Ascites and $L_{1210}$ leukemia which comprises administering to a host afflicted with said tumor an amount of a compound according to claim 1 sufficient to inhibit the growth of said tumor, together with an inert pharmaceutically acceptable carrier.

19. A method according to claim 18, wherein the compound is administered intraveneously.

20. A method according to claim 18, wherein said compound is a miture of the α-anomers of (−)daunosaminyl(−)4-demethoxydaunomycinone and (−)daunosaminyl(+)4-demethoxydaunomycinone.

* * * * *